(12) United States Patent
Lazzari et al.

(10) Patent No.: US 7,034,069 B2
(45) Date of Patent: Apr. 25, 2006

(54) HIGH MOLECULAR WEIGHT HYDROXYPHENYLBENZOTRIAZOLE UV-ABSORBERS FOR THIN FILM APPLICATIONS

(75) Inventors: Dario Lazzari, Bologna (IT); Gianluca Ferri, Anzola Emilia (IT); Massimiliano Sala, Modena (IT); Michela Bonora, Bologna (IT); Manuele Vitali, Bologna (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 108 days.

(21) Appl. No.: 10/482,522

(22) PCT Filed: Jun. 24, 2002

(86) PCT No.: PCT/EP02/06958

§ 371 (c)(1),
(2), (4) Date: Dec. 29, 2003

(87) PCT Pub. No.: WO03/004490

PCT Pub. Date: Jan. 16, 2003

(65) Prior Publication Data

US 2004/0209981 A1    Oct. 21, 2004

(30) Foreign Application Priority Data

Jul. 2, 2001    (EP)    ................... 01810643

(51) Int. Cl.
| | | |
|---|---|---|
| C08K 5/3492 | (2006.01) | |
| C08K 5/34 | (2006.01) | |
| C09K 15/30 | (2006.01) | |
| A61J 1/10 | (2006.01) | |
| C07D 251/50 | (2006.01) | |

(52) U.S. Cl. .............. 524/91; 524/102; 524/103; 524/130; 524/140; 524/291; 544/198; 544/209

(58) Field of Classification Search ............ 524/91, 524/102, 103, 130, 140, 291; 544/198, 209

See application file for complete search history.

(56) References Cited

U.S. PATENT DOCUMENTS

| | | | | |
|---|---|---|---|---|
| 4,418,002 A | | 11/1983 | Zannucci et al. | ............ 252/403 |
| 4,929,250 A | * | 5/1990 | Hung et al. | .................... 8/507 |
| 5,700,394 A | * | 12/1997 | Isharani et al. | ........ 252/301.21 |
| 5,744,127 A | * | 4/1998 | Giuseppe et al. | ............. 424/59 |
| 6,361,764 B1 | * | 3/2002 | Richard et al. | ............... 424/59 |
| 2002/0010179 A1 | | 1/2002 | Richard et al. | ............. 514/245 |

FOREIGN PATENT DOCUMENTS

| | | |
|---|---|---|
| FR | 2757163 | 6/1998 |
| WO | 98/25922 | 6/1998 |

* cited by examiner

*Primary Examiner*—Kriellion Sanders
(74) *Attorney, Agent, or Firm*—Tyler A. Stevenson

(57) ABSTRACT

The present invention relates to highly compatible, high molecular weight hydroxyphenylbenzotriazole UV-absorbers and for their use in protecting plants in green houses and the protection of foodstuffs, beverages, pharmaceuticals, cosmetics, personal care products, shampoos and the like from the deleterious effects of ultraviolet radiation. It has been found that certain highly compatible, high molecular weight hydroxyphenylbenzotriazole UV-absorbers are especially effective towards this end when incorporated in the containers or films in which such materials are stored.

15 Claims, No Drawings

HIGH MOLECULAR WEIGHT HYDROXYPHENYLBENZOTRIAZOLE UV-ABSORBERS FOR THIN FILM APPLICATIONS

The present invention relates to highly compatible, high molecular weight hydroxyphenylbenzotriazole UV-absorbers and for their use in protecting plants in green houses and the protection of foodstuffs, beverages, pharmaceuticals, cosmetics, personal care products, shampoos and the like from the deleterious effects of ultraviolet radiation. It has been found that certain highly compatible, high molecular weight hydroxyphenylbenzotriazole UV-absorbers are especially effective towards this end when incorporated in the containers or films in which such materials are stored.

It is well known in the art that some types of crops are degraded by the UV-components of solar radiation which must be filtered off to obtain high quality and productivity of the crops. Additionally, some microorganisms, e.g. Botrytis Cinerea, as well as some harmful insects, e.g. white flies, aphides, thrips or leafminers, can proliferate under specific UV-irradiation. These pest can be significantly reduced when UV light does not or to less extent reach the plants. [R. Reuveni et al., *Development of photoselective PE films for control of foliar pathogens in greenhouse-grown crops, Plasticulture No.* 102, p. 7 (1994); Y. Antignus et al, *The use of UV absorbing plastic sheets to protect crops against insects and spread of virus diseases, CIPA Congress March* 1997, pp. 23–33]. On the other hand, bee activity, requiring a certain band of UV radiation, needs to be retained in greenhouses in order to ensure fructification on flowering plants, e.g. tomato, cucumber, pumpkin etc.

Also many packaged products such as certain fruit juices, soft drinks, beer, wines, food products, dairy products, cosmetics, shampoos, vitamins and pharmaceuticals are deleteriously affected, i.e. degraded, by the effects of ultraviolet (UV) light when packaged in plastic containers which allow the transmission of such light.

The use of UV absorbers towards protecting bottle and film contents is well known. However there is a trend towards the use of clear or lightly colored containers. More aesthetically pleasing containers may be formed from clear plastics which also allow one to view the contents. Unfortunately, clear and lightly colored containers and films allow the transmission of significant portions of ultraviolet light, i.e. light in the range of about 280 to about 400 nm. Further, there is a trend towards more light-weight and hence thinner walled containers.

Thin-walled containers, by virtue of a shorter path length, will allow more UV light to pass. Due to these trends in packaging there is a need for more efficient UV absorbers for use in this area.

Many cooking oils and salad oils are now offered in clear PET [poly(ethylene terephthalate)] packaging. Practically all vegetable or seed-based oils such as soybean, olive, safflower, cottonseed and corn oils contain varying levels of unsaturated olefinic acids or esters (e.g. linoleates) which are susceptible to light-induced degradation. Most plant based oils also contain natural chlorophyll or other pigment photosensitizers. Pascall, et al., *J. Food Sci.*, 60 (5), 1116 (1995), discuss the UV protection of soybean oil with the use of Tinuvin® 326 incorporated into coextruded, multi-layered, polypropylene-based containers. Tinuvin® 326 is a benzotriazole UV absorber, 5-chloro-2-(2-hydroxy-3-tert-butyl-5-methylphenyl)-2H-benzotriazole, available from Ciba Specialty Chemicals Corp.

The instant high molecular weight hydroxyphenylbenzotriazole UV-absorbers show excellent compatibility and persistence in a variety of plastic materials. The same time, these UV absorbers provide efficient and selective UV shielding for in greenhouse films and packaging materials. Due to their high molecular weight they are highly compatible with many polymers, allowing thus to incorporate higher amounts of UVA. They are thermally stable and do not exude from the polymer, which is important when in contact with food or beverages.

The present invention relates to hydroxyphenylbenzotriazole UV-absorbers of formula (I) or (II)

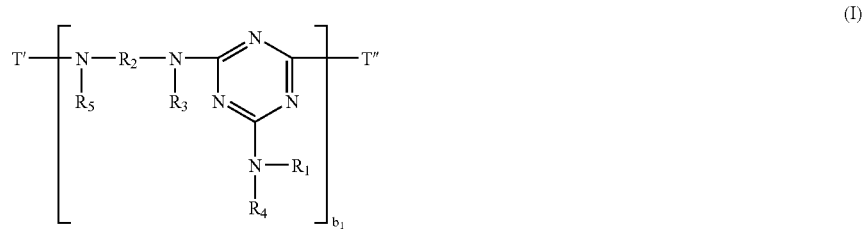

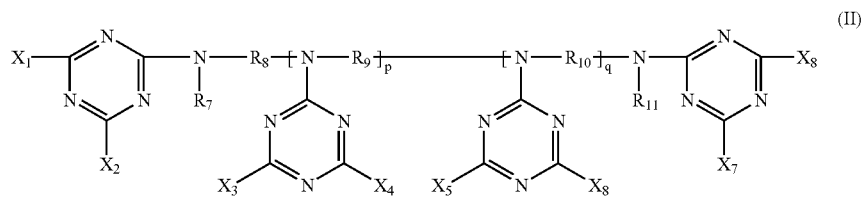

wherein in formula (I)

$R_1$, $R'_1$, $R_3$ and $R_5$ independently of one another are hydrogen, $C_1$–$C_{12}$alkyl, $C_5$–$C_{12}$cycloalkyl, $C_1$–$C_4$-alkyl-substituted C5–$C_{12}$cycloalkyl, phenyl, phenyl which is substituted by —OH and/or $C_1$–$C_{10}$alkyl; $C_7$–$C_9$phenylalkyl or $C_7$–$C_9$phenylalkyl which is substituted on the phenyl radical by —OH and/or $C_1$–$C_{10}$alkyl;

$R_4$ is a group of formula (III)

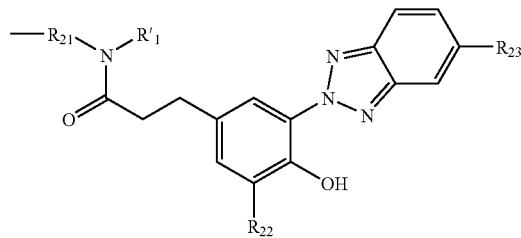

$R_2$ and $R_{21}$, are independently $C_2$–$C_{18}$alkylene, $C_5$–$C_7$cycloalkylene or $C_1$–$C_4$alkylene-di($C_5$–$C_7$cyclo or the radicals $R_5$, $R_2$ and $R_3$, together with the nitrogen atoms to which they are bound, perform a 5- to 10-membered heterocyclic ring, $b_1$ is a number from 2 to 50, $R_{22}$ is is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_{22}$ is alkyl of 1 to 24 carbon atoms substituted by one or two hydroxy groups;

$R_{23}$ is hydrogen or halogen;

the terminal group T' is hydrogen or a group

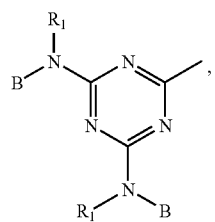

wherein B is a group of formula (III) and
the terminal group T' is

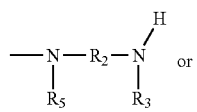

or

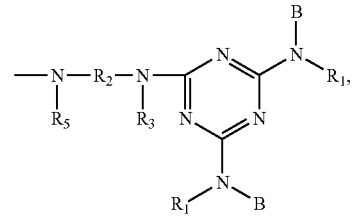

wherein in formula (II)

p and q are independently 0, 1 or 2;

with the proviso, that if p and q are both zero $X_1$, $X_2$, $X_7$ and $X_8$ are a group of formula —$NR_1B$;

$R_7$, $R_{11}$, $R_{12}$ and $R_{13}$ independently of one another are hydrogen or $C_1$–$C_{12}$alkyl, $R_8$, $R_9$ and $R_{10}$ independently of one another are $C_2$–$C_{10}$alkylene, and $X_1$, $X_2$, $X_3$, $X_4$, $X_5$, $X_6$, $X_7$ and $X_8$ independently of one another are a group —$NR_{12}R_{13}$ or —$NR_1B$ wherein B is a group of the formula (III) as defined above;

with the proviso that at least one triazine ring is substituted with a group —$NR_1B$.

Preferably at least two and more preferably at least three, most preferably at least four of $X_1$ to $X_8$ are a group —$NR_1B$.

Halogen is fluoro, chloro, bromo or iodo, chloro is preferred.

The alkyl groups may be linear or branched. Examples of alkyl having up to 24 carbon atoms are methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl and docosyl.

Examples of $C_5$–$C_{12}$cycloalkyl are cyclopentyl, cyclohexyl, cycloheptyl, cyclooctyl and cyclododecyl. $C_5$–$C_8$Cycloalkyl, especially cyclohexyl, is preferred.

$C_1$–$C_4$Alkyl-substituted $C_5$–$C_{12}$cycloalkyl is for example methylcyclohexyl or dimethylcyclohexyl.

—OH— and/or $C_1$–$C_{10}$alkyl-substituted phenyl is for example methylphenyl, dimethylphenyl, trimethylphenyl, tert-butylphenyl or 3,5-di-tert-butyl-4-hydroxyphenyl.

Examples of $C_7$–$C_9$phenylalkyl are benzyl and phenylethyl.

$C_7$–$C_9$Phenylalkyl which is substituted on the phenyl radical by —OH and/or by alkyl having up to 10 carbon atoms is for example methylbenzyl, dimethylbenzyl, trimethylbenzyl, tert-butylbenzyl or 3,5-di-tert-butyl-4-hydroxybenzyl.

Examples of alkenyl having up to 24 carbon atoms are allyl, 2-methallyl, butenyl, pentenyl and hexenyl. Allyl is preferred. The carbon atom in position 1 is preferably saturated.

Examples of alkylene having up to 24 carbon atoms are methylene, ethylene, propylene, trimethylene, tetramethylene, pentamethylene, 2,2-dimethyltrimethylene, hexamethylene, trimethylhexamethylene, octamethylene and decamethylene.

An example of $C_5–C_7$cycloalkylene is cyclohexylene.

An example of $C_1–C_4$alkylenedi($C_5–C_7$cycloalkylene) is methylenedicyclohexylene.

Where the radicals $R_5$, $R_2$ and $R_3$, together with the nitrogen atoms to which they are attached, form a 5- to 10-membered heterocyclic ring, this ring is for example

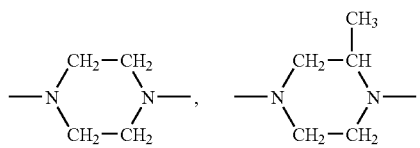

A 6-membered heterocyclic ring is preferred.

Preferably in the group of formula (III) $R_{22}$ is hydrogen, $C_7–C_9$phenylalkyl or $C_1–C_8$alkyl, particularly preferred is tert butyl.

Preferably $R_1$, $R'_1$, $R_3$ and $R_5$ independently of one another are hydrogen, $C_1–C_{12}$alkyl or $C_5–C_6$cycloalkyl, more preferably hydrogen or $C_1–C_6$alkyl.

Preferably $R_2$ and $R_{21}$ independently are $C_2–C_8$alkylene.

Preferably $R_3$ and $R_5$ have the same meaning.

b1 is preferably a number from 2 to 25 and more preferably from 2 to 20.

Preferably $R_7$ and $R_{11}$ independently are hydrogen or $C_1–C_4$alkyl and $R_8$, $R_9$ and $R_{10}$ are $C_2–C_4$alkylene.

In general compounds of formula (I) are preferred.

The compounds described above under formula (I) and (II) and under formula (III) are essentially known and commercially available. All of them can be prepared by known processes.

The preparation of the compounds of formula (I) and (II) can be done in analogy to the processes disclosed, for example, in U.S. Pat. No. 5,679,733, U.S. Pat. No. 3,640,928, U.S. Pat. No. 4,198,334, U.S. Pat. No. 5,204,473, U.S. Pat. No. 4,619,958, U.S. Pat. No. 4,110,306, U.S. Pat. No. 4,110,334, U.S. Pat. No. 4,689,416, U.S. Pat. No. 4,408,051, SU-A-768,175 (Derwent 88–138,751/20), U.S. Pat. No. 5,049,604, U.S. Pat. No. 4,769,457, U.S. Pat. No. 4,356,307, U.S. Pat. No. 4,619,956, U.S. Pat. No. 5,182,390, GB2,269,819, U.S. Pat. No. 4,292,240, U.S. Pat. No. 5,026,849, U.S. Pat. No. 5,071,981, U.S. Pat. No. 4,547,538, U.S. Pat. No. 4,976,889, U.S. Pat. No. 4,086,204, U.S. Pat. No. 6,046,304, U.S. Pat. No. 4,331,586, U.S. Pat. No. 4,108,829, U.S. Pat. No. 5,051,458, WO-A-94/12,544 (Derwent 94–177,274/22), DD-A-262,439 (Derwent 89–122,983/17), U.S. Pat. No. 4,857,595, U.S. Pat. No. 4,529,760, U.S. Pat. No. 4,477,615, CAS 136,504-96-6, U.S. Pat. No. 4,233,412, U.S. Pat. No. 4,340,534, WO-A-98/51,690 and EP-A-1,803.

The preparation of the precursor of the compunds according to formula (III) is for example disclosed in EP-A-057 160. From the ester disclosed therein the amide can be made by conventional methods.

A general procedure to obtain a compound of formula (I) is outlined below.

A diaminic starting material is reacted with an appropriate cyanuric dichloride bringing a benzotriazole active moiety as a substituent to the aromatic ring.

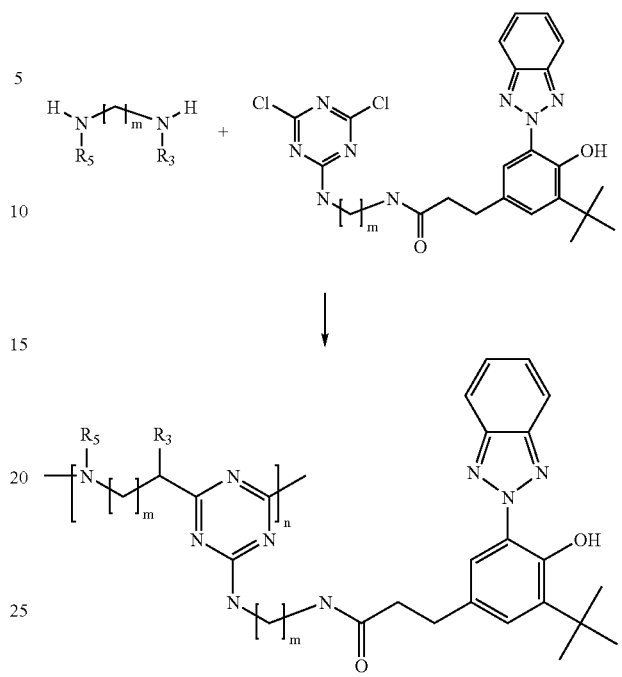

The reaction is carried out in the usual organic solvents especially toluene, xylene, mesitylene are suitable. The temperature of the polymerization reaction may vary from room temperature to 200° C., preferred is the range 120–170° C.

As a base NaOH, KOH, $K_2CO_3$, $Na_2CO_3$ are useful, carbonates are especially useful.

Alternatively the reaction can be carried out polymerizing trichlorotriazine and a diaminic starting material.

A schematic representation of the reaction is for example:

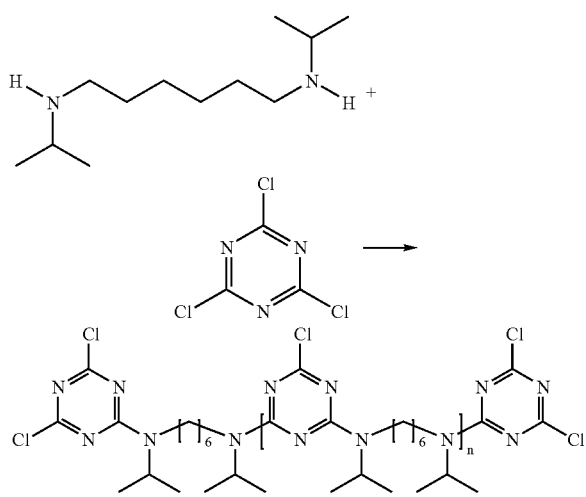

cyanuric chloride is used in for example 10% excess. The reaction is carried out in the usual organic solvents, examples are already mentioned. The polymerization temperature is as given above.

The highly reactive chlorinated back bone is then functionalized with a suitable benzotriazole UV-absorber such as for example

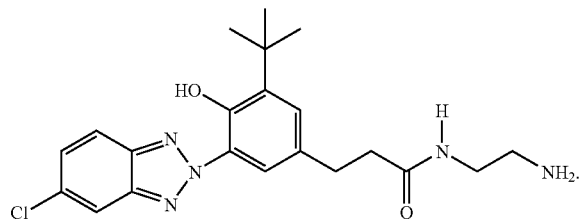

The preparation of suitable benzotriazoles is mentioned above.

A further subject of the invention is a plastic container or film which protects against the deleterious effects of ultraviolet radiation which comprise
(a) a clear or lightly colored plastic, and
(b) a compound of formula (I) or formula (II).

Definitions and preferences for the compounds of formula (I) and (II) have been already given and apply also for this subject of the invention.

The compounds are useful for many kinds of plastic materials from which containers and films can be made. Examples are given below.

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndio-tactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactc polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α, β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

19. Polycarbonates and polyester carbonates.

20. Polyketones.

21. Polysulfones, polyether sulfones and polyether ketones.

22. Blends of the aforementioned polymers (polyblends), for example PP/EPDM, Polyamide/EPDM or ABS, PVC/EVA, PVC/ABS, PVC/MBS, PC/ABS, PBT/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferred is a plastic container or film wherein the clear or lightly colored plastic is a polyolefin, a polyester, a polyvinylalcohol, a polyvinylacetate or a polycarbonate.

More preferred are polyethylenetherephthalate (PET) and polyolefins, in particular (PE), polyethylene, (LDPE), low density polyethylene, linear low density polyethylene (LLDPE), (VLDPE) and (ULDPE).

It is preferred that the plastic container or film is a food packaging material.

Preferably the thickness of the film is from 10μ to 200μ more preferably from 20μ to 80μ and in particular from 20μ to 60μ and the thickness of the plastic container from 200μ to 1000μ.

Preferred is a plastic container or film wherein the compound of formula (I) or (II) is present in an amount of from 0.005% to 10% more preferably of from 0.05% to 4% and most preferably of from 0.1% to 2.5%.

Alongside the stabilizer of the formula (I) or (II) the container or film of the invention may also include other stabilizers or other additives, such as a phenolic antioxidant, a sterically hindered amine and/or a phosphite or phosphonite.

The plastic container or film may additionally contain an iron based additive as oxygen absorber.

Examples for further stabilizers and additives are given below.

1. Antioxidants 1.1. Alkylated monophenols, for example 2,6-di-tert-butyl-4-methylphenol, 2-tert-butyl-4,6-dimethylphenol, 2,6- di-tert-butyl-4-ethylphenol, 2,6-di-tert-butyl-4-n-butylphenol, 2,6-di-tert-butyl- 4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis-(2,6di-tert-butylphenol, 4,4'-methylenebis(6-tert-butyl-2-methylphenol), 1,1-bis(5-tert-butyl-4-hydroxy-2methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy- 2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methy-phenyl)dicyclopentadiene, bis[2-(3'-tert-butyl-2'-hydroxy-5'-methylbenzyl-6-tert-butyl-4-methylphenyl]terephalate, 1,1-bis-(3, 5dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1, 5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris (3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4, 6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxbenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl4hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tertbutyl-4-hydroxyphenylpropionyl)trimethylenediamide, N,N'-bis(3,5di-tert-butyl-4-hydroxyphenylpropionyl)-hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)-propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyidiphenylamines, a mixture of mono- and dialkylated isopropyl/isohexyldiphenylamines, a mixture of mono- and dialkylated tert-butyldiphenylamines, 2,3-dihydro-3,3-di-methyl-4H-1,4benzothiazine, phenothiazine, a mixture of mono- und dialkylated tert-butyl/-tert-octylphenothiazines, a mixture of mono- and dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethylphenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—$CH_2CH_2$—COO—$CH_2CH_2$—]$_2$— where R=3'-tert-butyl-4'hyddroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris (2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl) 2-n-butyl-2-(2-hydroxy-3,5-di-tert-butylbenzyl)-malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl)succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl1-oxa-3,8-diaza-4-oxospiro[4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl4-piperidyl) hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-di-substituted oxanilides and mixtures of o- and p-ethoxy-di-substituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz-[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-di-benz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl (3,3 ', 5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:

Tris(2,4-di-tert-butylphenyl) phosphite (Irgafos® 168, Ciba-Geigy), tris(nonylphenyl) phosphite,

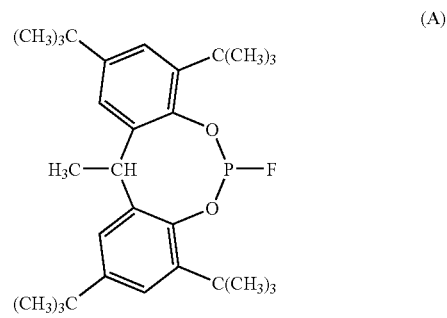

(A)

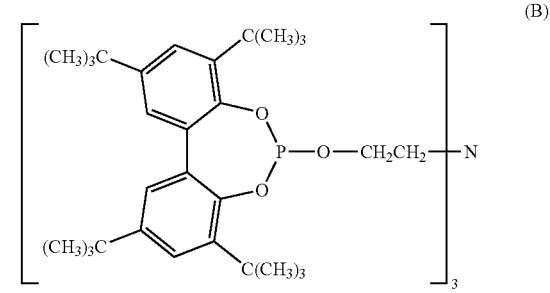

(B)

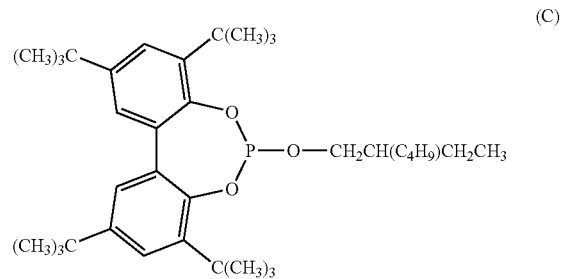

(C)

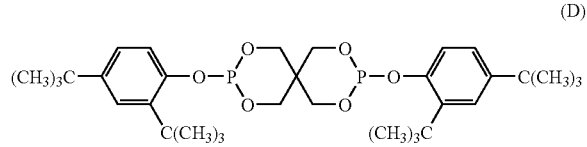

(D)

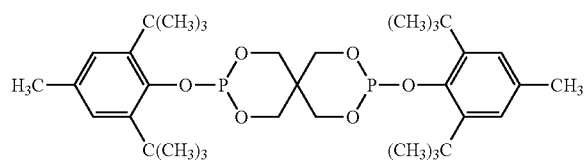

(E)

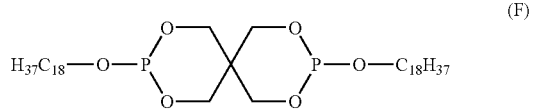

(F)

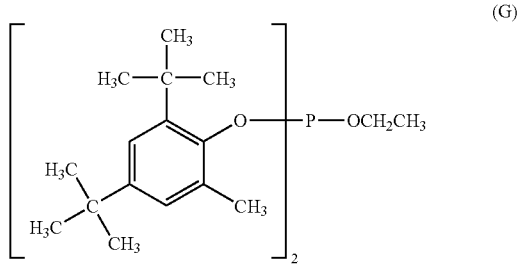

(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of βthiodipropionic acid, for example the lauryl, stearyl, myristyl or tridecyl esters, mercaptobenzimidazole or the zinc salt of 2-mercaptobenzimidazole, zinc dibutyidithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'dimethylbenzylidene)sorbitol, 1,3:2,4-di(paramethyldibenzylidene)sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents, oxygen absorbers and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A4316611; DE-A4316622; DE-A4316876; EP-A-0589839 or EP-A-0591102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilizers added are determined by the nature of the substrate to be stabilized and its intended use; in many cases from 0.1 to 5% by weight is used, based on the polymer to be stabilized.

Preferably sterically hindered amines such as for example mentioned under item 2.6 are additionally present.

The additives of the invention and optional further components may be added to the polymer material individually or mixed with one another. If desired, the individual components can be mixed with one another before incorporation into the polymer for example by dry blending, compaction or in the melt.

The incorporation of the additives of the invention and optional further components into the polymer is carried out by known methods such as dry blending in the form of a powder, or wet mixing in the form of solutions, dispersions or suspensions for example in an inert solvent, water or oil. The additives of the invention and optional further additives may be incorporated, for example, before or after molding or also by applying the dissolved or dispersed additve or additive mixture to the polymer material, with or without subsequent evaporation of the solvent or the suspension/dispersion agent. They may be added directly into the processing apparatus (e.g. extruders, internal mixers, etc), e.g. as a dry mixture or powder or as solution or dispersion or suspension or melt.

The incorporation can be carried out in any heatable container equipped with a stirrer, e.g. in a closed apparatus such as a kneader, mixer or stirred vessel. The incorporation is preferably carried out in an extruder or in a kneader. It is immaterial whether processing takes place in an inert atmosphere or in the presence of oxygen.

The addition of the additive or additive blend to the polymer can be carried out in all customary mixing machines in which the polymer is melted and mixed with the additives. Suitable machines are known to those skilled in the art. They are predominantly mixers, kneaders and extruders.

The process is preferably carried out in an extruder by introducing the additive during processing.

Particularly preferred processing machines are single-screw extruders, contrarotating and corotating twin-screw extruders, planetary-gear extruders, ring extruders or cokneaders. It is also possible to use processing machines provided with at least one gas removal compartment to which a vacuum can be applied.

Suitable extruders and kneaders are described, for example, in *Handbuch der Kunststoffextrusion, Vol. 1 Grundlagen*, Editors F. Hensen, W. Knappe, H. Potente, 1989, pp. 3–7, ISBN:3-446-14339-4 (*Vol. 2 Extrusionsanlagen* 1986, ISBN 3-446-14329-7).

For example, the screw length is 1–60 screw diameters, preferably 35–48 screw diameters. The rotational speed of the screw is preferably 10–600 rotations per minute (rpm), very particularly preferably 25–300 rpm.

The maximum throughput is dependent on the screw diameter, the rotational speed and the driving force. The process of the present invention can also be carried out at a level lower than maximum throughput by varying the parameters mentioned or employing weighing machines delivering dosage amounts.

If a plurality of components are added, these can be premixed or added individually. The additives of the invention and optional further additives can also be sprayed onto the polymer material. They are able to dilute other additives (for example the conventional additives indicated above) or their melts so that they can be sprayed also together with these additives onto the material. Addition by spraying during the deactivation of the polymerization catalysts is particularly advantageous; in this case, the steam evolved may be used for deactivation of the catalyst. In the case of spherically polymerized polyolefins it may, for example, be advantageous to apply the additives of the invention, optionally together with other additives, by spraying.

The additives of the invention and optional further additives can also be added to the polymer in the form of a masterbatch ("concentrate") which contains the components in a concentration of, for example, about 1% to about 40% and preferably 2% to about 20% by weight incorporated in a polymer. The polymer must not be necessarily of identical structure than the polymer where the additives are added finally. In such operations, the polymer can be used in the form of powder, granules, solutions, suspensions or in the form of latices.

Incorporation can take place prior to or during the shaping operation, or by applying the dissolved or dispersed compound to the polymer, with or without subsequent evaporation of the solvent. In the case of elastomers, these can also be stabilized as latices. A further possibility for incorporating the additives of the invention into polymers is to add them before, during or directly after the polymerization of the corresponding monomers or prior to crosslinking. In this context the additive of the invention can be added as it is or else in encapsulated form (for example in waxes, oils or polymers).

In a specific embodiment the plastic container or film is a multilayer construction of between 2 and 7 polymer layers containing the compound of formula (I) or (II) in at least 1 layer.

In this case a polymer composition of the invention containing a relatively large amount of stabilizer of the formula (I) or (II), for example 1–15% by weight, is applied in a thin layer (10–20μ) to a shaped article made from a polymer containing little or no stabilizer of the formula (I) or (II). Application can be made at the same time as the shaping of the base article, for example by coextrusion. Alternatively, application can be made to the base article after it has been shaped, for example by lamination with a film or by coating with a solution. The external layer or layers of the finished article has or have the function of a UV filter which protects the interior of the article against UV light.

Still a further subject of the invention is the use of a compound of formula (I) which is incorporated into a plastic container or film, for content protection of greenhouses or packaged foodstuffs beverages, pharmaceuticals, cosmetics or personal care products.

Content protection of packaged foodstuffs, beverages, pharmaceuticals, cosmetics or personal care products is preferred.

The following examples illustrate the invention.

A PREPARATION EXAMPLES

Example A1

1.1 Preparation of the Compound of Formula 101:

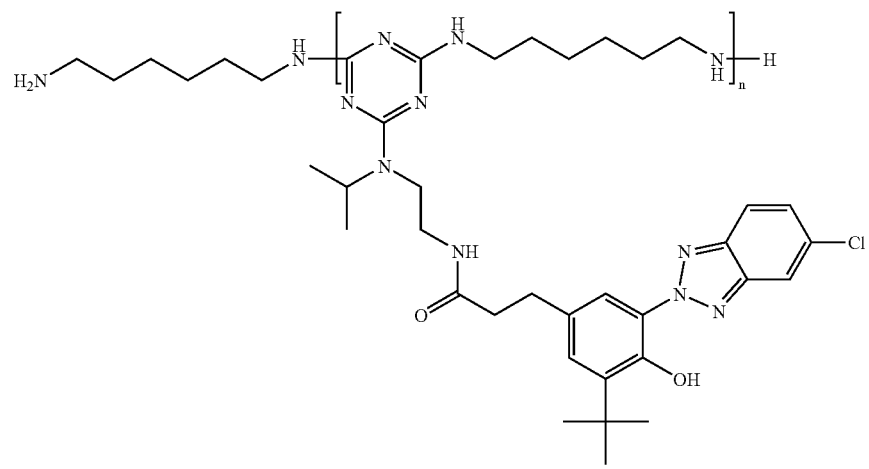

35.6 g (0.059 mol) of the compound of Example 1.2, and 7.5 g (0.0649 mol) of hexamethylendiamine in 100 ml of mesithylene are charged into a three-necked, round-bottomed flask equipped with a mechanical stirrer and a condenser. The mixture is stirred at 90° C. for 3 hours, then the temperature is dropped to room temperature and 20 g of a 30% solution of NaOH are added; after that the reaction is allowed to react for 22 hours at 160° C. and the water is azeotropically distilled off. The organic solution is filtered off, washed with water and concentrated under reduced pressure. 18.7 g of a white solid are recovered, melting point 140° C., n is 4.5.

1.2 Preparation of the Intermediate of Formula:

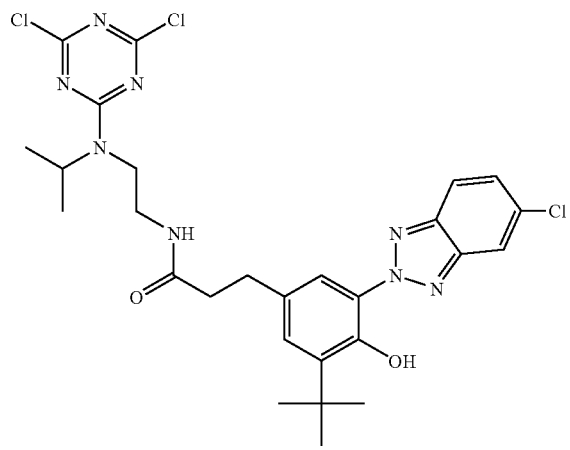

To a solution 12.9 g (0.070 mol) of cyanuric chloride in 100 ml of toluene a solution of 32.9 g (0.007 mol) of the compound of the example 1.3 in 200 mol toluene are slowly added. The mixture is maintained at 60° C. for 2 hours then 15.4 g of a 20% solution of NaOH are added at room temperature and the reaction is allowed to react for 10 hours at 60° C. The organic layers are washed with water at room temperature, dried with sodium sulfate, filtered off and concentrated under vacuum. 36.6 g of a pale white solid is obtained and the structure is confirmed by NMR.

1.3 Preparation of the Intermediate of Formula:

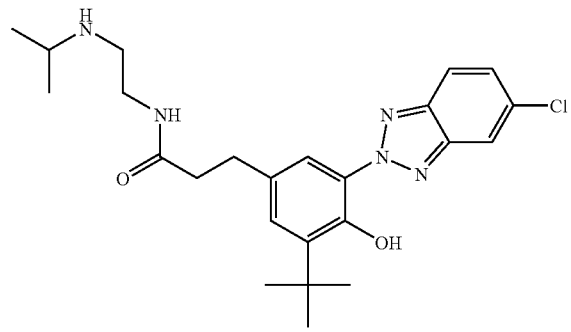

In an autoclave 35.0 g (0.084 mol) of the compound of Example 1.4, 100 ml of methanol, 7.3 g (0.1265 mol) of acetone and 1.7 g of 5% Pt on carbon are added and 20 bar of hydrogen are charged. The reaction is allowed to react for 20 hours at room temperature. The solution is filtered off and concentrated under vacuum. 37.7 g of a pale yellow solid are recovered (melting range: 127.6–140.5° C.).

1.4 Preparation of the Intermediate of Formula:

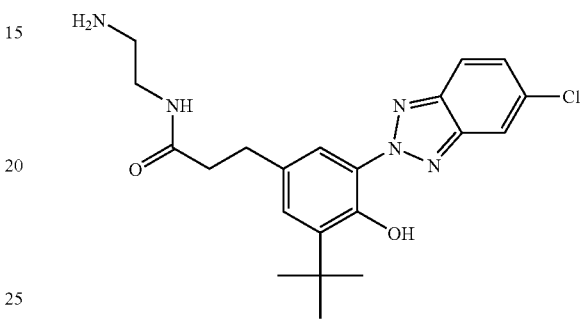

60.6 g (0.155 mol) of 3-[3-.tert.-Butyl-5-(5-chloro-benzotriazol-2-yl)-4-hydroxy-phenyl]-propionic acid ethyl ester are added to 250 ml of ethylendiamine. The temperature is increased to 80° C. and the solution is allowed to react for 6 hours. The organic solution is then concentrated under vacuum in order to eliminate the excess of ethylendiamine. Using a mixture of $CH_2Cl_2$/hexane for recrystallisation a solid is precipitated and dried under vacuum. 45.0 g of a white solid are recovered (melting range: 156.6°–168.8° C.).

Example A2

Following the procedure outlined in example 1.1 compound 102 of following structure is obtained.

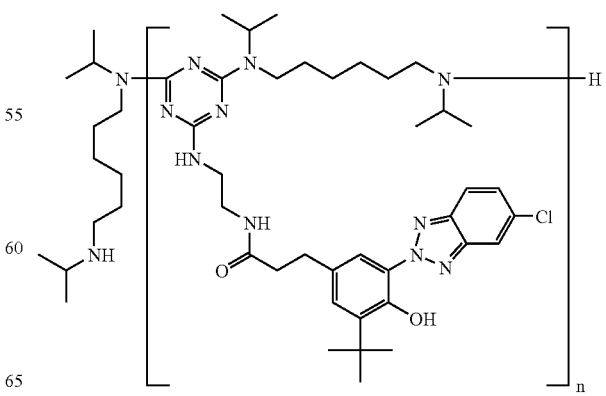

The compound is a pale yellow powder (melting range 159–172°C.), n is 6.

Example A3

3.1 Preparation of the Intermediate of Formula:

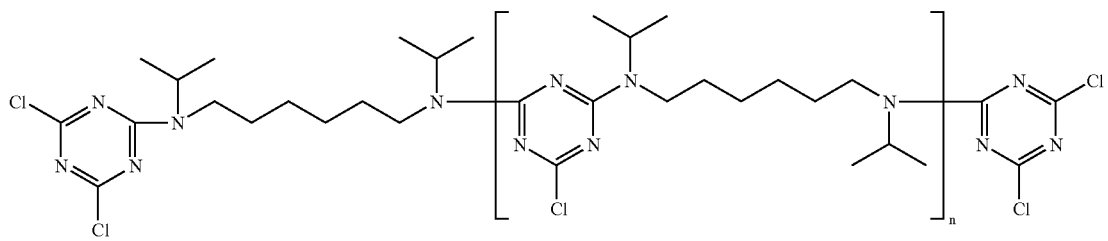

To a solution of 24.3 g. (0.131 mole) of cyanuric chloride in 150 ml of toluene, 24 g (0.119 mole) of N,N' diisopropylhexamethylenediamine at −10° C. are slowly added, keeping the temperature during the addition .

The temperature is raised to 20° C.; after 1 hour the mixture is cooled to 0° C. and an aqueous solution of 20 g. (0.144 moles) of potassium carbonate in 40 ml of water, is added.

The mixture is then heated slowly to 75° C. for 3 hours, and the water is azeotropically distilled off, under vacuum.

When the mixture is anhydrous, it is cooled down to room temperature, and filtered off. The solution is concentrated under vacuum and a white solid of 27 g. is obtained. The structure has been confirmed by NMR.

3.2 Preparation of the Compound of Formula 103:

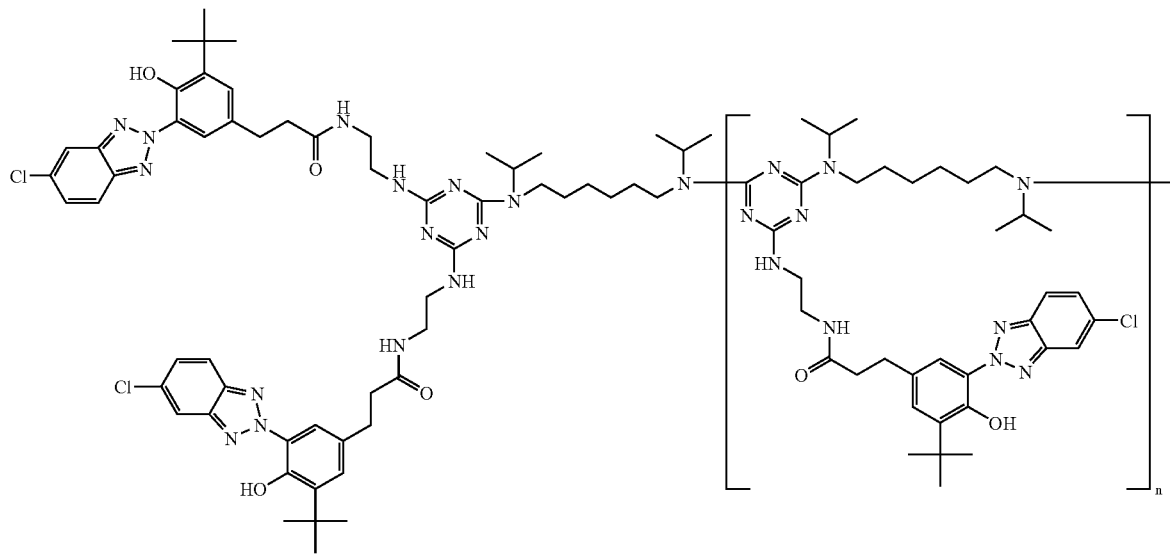

-continued

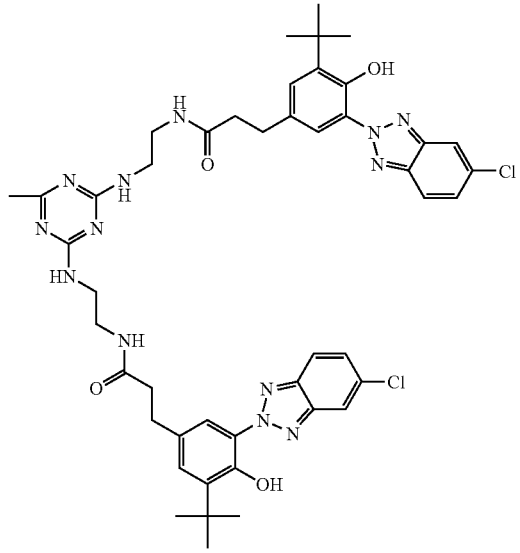

To a solution of 21 g. (0.085 moles) of the intermediate of example 3.1 in 100 ml of trimethylbenzene heated to 75° C., 35.3 g. (0.085 moles) of .N.-(2-Amino-ethyl)-3-[3-.tert.-butyl-5-(5-chloro-benzotriazol-2-yl)-4-hydroxyphenyl]-propionamide are slowly added. The temperature is raised to 160° C. for 90 minutes, and then, decreased to 40° C.

An aqueous solution of 8.5 g.(0.085 moles) of sodium hydroxide in 10 ml of water, is added. The mixture is heated to 160° C. for 1 hour, and the water is azeotropically distilled off.

After cooling to 20° C., the mixture is filtered and concentrated under vacuum, to obtain a pale yellow solid of 45 g (melting range 175.2°–180.5° C.), n is 5.5.

Example A4

4.1 Preparation of the Intermediate of Formula:

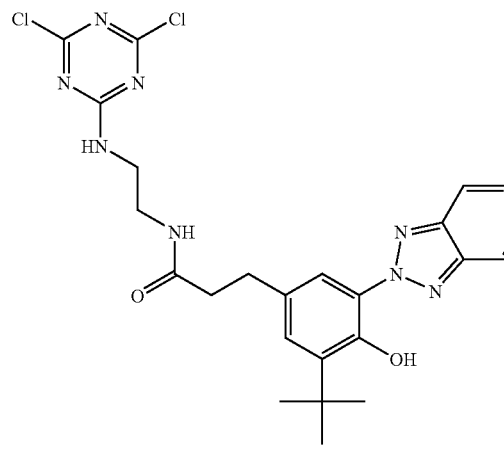

Following the procedure reported in example 1.2 and using as reagent, the compound of the example 1.4, the intermediate in the formula above has been obtained. The structure has been confirmed by NMR.

4.2 Preparation of the Intermediate of Formula:

To a solution of 42.8 g (0.076 mol) of the intermediate of the example 4.1 in 100 ml of toluene, 9.82 g (0.076 mol) of dibutylamine are slowly added. The reaction mixture is heated to 70° C. for half an hour and then cooled to room temperature. A solution of 11.5 g (0.083 mol) of potassium carbonate in 23 ml of water is added. The temperature is then raised to 70° C. for 3 hours. The mixture reaction is washed twice with water keeping the temperature at 70° C. The residual water is then azeotropically distilled off. The mixture is cooled to room temperature and the precipitate filtered off and dried in the oven under vacuum. A pale yellow powder is obtained. The structure is confirmed by NMR.

4.3 Preparation of the Product of Formula 104:

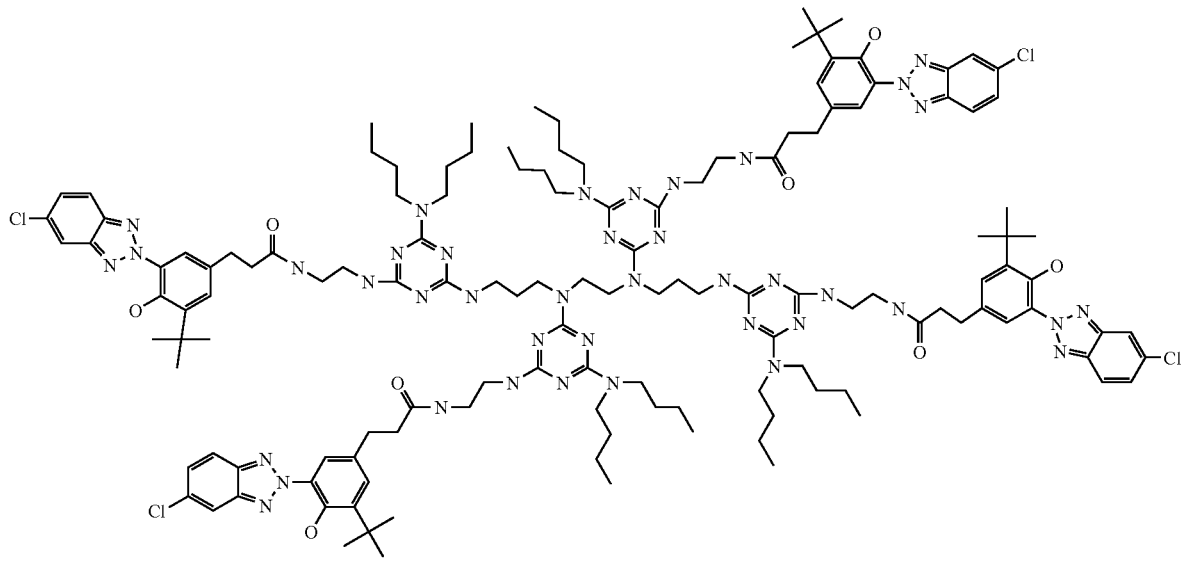

32.3 g (0.0491 mol) of the intermediate of example 4.2 dissolved in 150 ml of toluene and 2.25 g (0.012 mol) of N1-[2-(3-Amino-propylamino)-ethyl]-propane-1,3-diamine were charged into an autoclave. The mixture is heated to 170° C. for one hour. After cooling to room temperature a solution of 2.1 g (0.054 mol) of NaOH in 4.2 ml of water is added. The mixture is heated again to 170° C. and kept there for additional three hours. The recovered solution is dried with sodium sulfate and concentrated under vacuum. A pale yellow powder is obtained (melting range 142–153° C.).

B APPLICATION EXAMPLES

Example B1

In order to evaluate the UV-absorber characteristics the compound 101 of example A1, when mixed with a commercial thermoplastic material, thin linear low density polyethylene (LLDPE) films were prepared, containing, as a typical formulation, 1% by weight of compound 101. The compound is mixed with milled LLDPE (Dowlex® NG 5056E, Dow Chemical), characterized by a density of 0.919 g/cm$^3$ and a melt flow index (190° C./2.1 Kg) of 1.1 and extruded at a maximum temperature of 230° C. in a OMC twin-screw extruder. The granules so obtained were blown in a lab-scale Formac blow-extruder at a maximum temperature of 230° C. to give a film of about 50 μm thickness. UV-Vis spectra were recorded in the range 200–800 nm by means of a Perkin-Elmer lambda 20 spectrophotometer, equipped with a RSA-PE-20 Labsphere integrating sphere. The film displays an absorption in the UV region, with a transmittance minimum of 27% at 354 nm and an average transmittance of 35% between 280 and 400 nm.

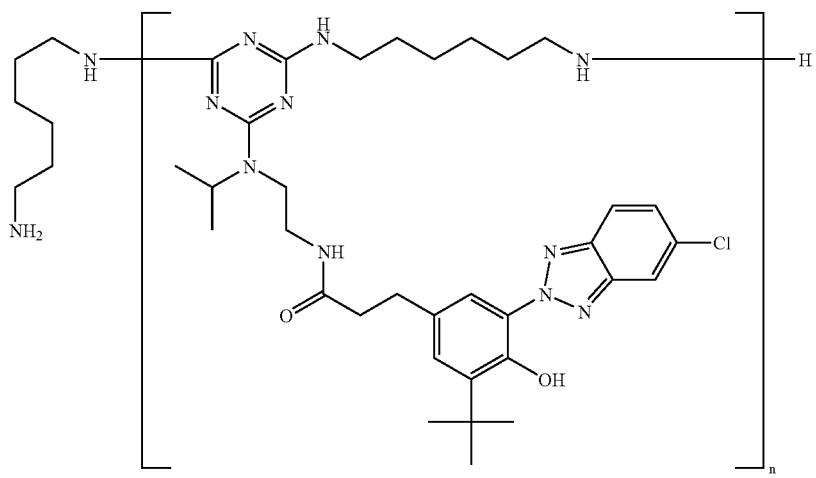

A second piece of film of the same composition is stored at room temperature inside an envelope and between two pieces of paper. The film is periodically inspected visually to verify possible exudation (blooming) of the compound from the bulk of the polymer matrix. After 1500 hours no blooming occurs.

Another piece of film of the same composition is exposed in a forced circulating air oven at 40° C. and inspected as above. After 1500 hours no blooming occurs.

Example B2 Using Compound 102 of Example A2

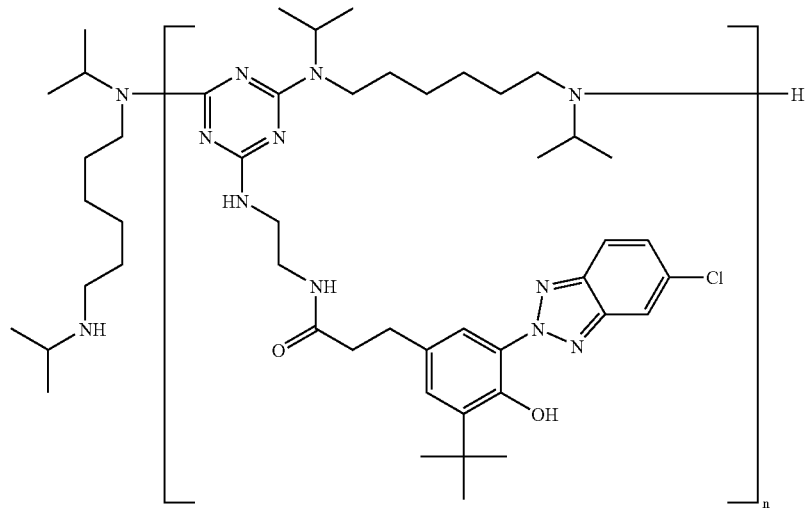

Thin LLDPE films are prepared as described in Example B1. They are 50 μm thick and contain 1% of the respective compound. UV-Vis spectra are recorded as described above. The films display an absorption in the UV region, with a transmittance minimum of 44% at 354 nm and an average transmittance of 51% between 280 and 400 nm.

The compatibility of the compound in LLDPE films is determined after exposure of the films at room temperature and at 40° C., as described in Example 1. After 1500 hours no blooming occurred in both cases.

Example B3 Using Compound 103 of Example A3

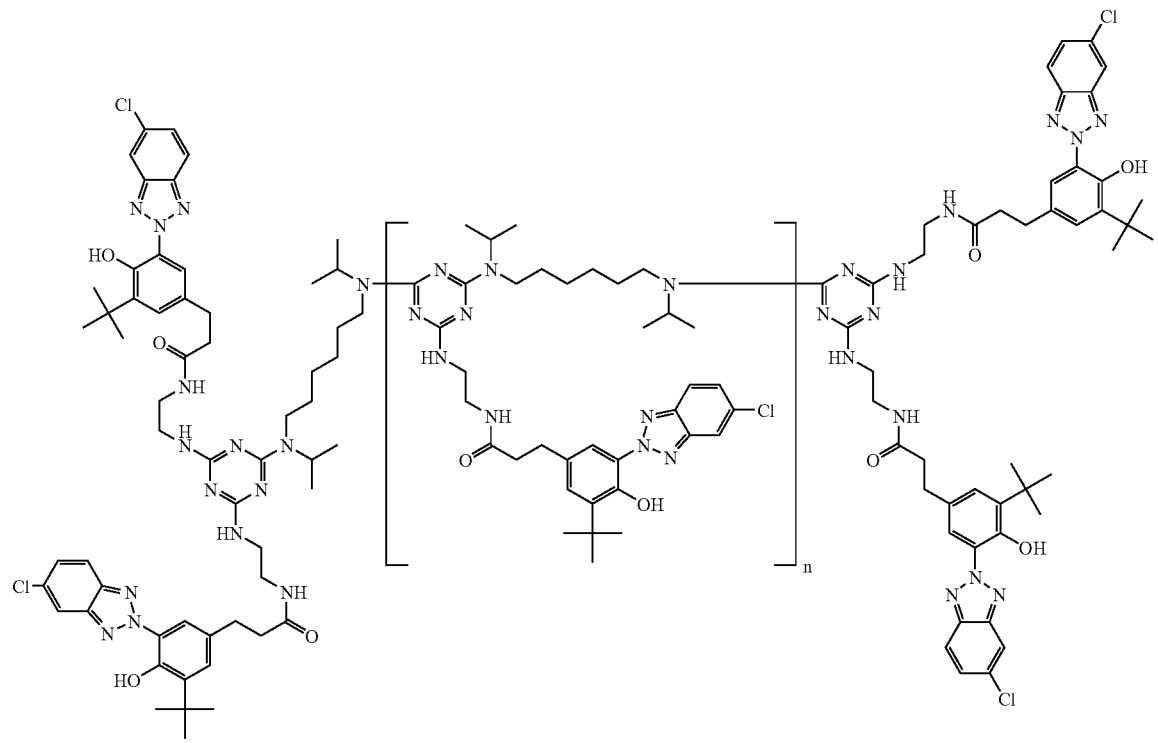

Thin LLDPE films are prepared as described in Example 1. They are 50 μm thick and contain 1% of the respective compound. UV-Vis spectra are recorded as described above. The films display an absorption in the UV region, with a transmittance minimum of 21% at 354 nm and an average transmittance of 30% between 280 and 400 nm.

The compatibility of the compound in LLDPE films is determined after exposure of the films at room temperature and at 40° C. as described in Example 1. After 1500 hours no blooming occurred in both cases.

What is claimed is:

1. A compound of formula (I) or (II),

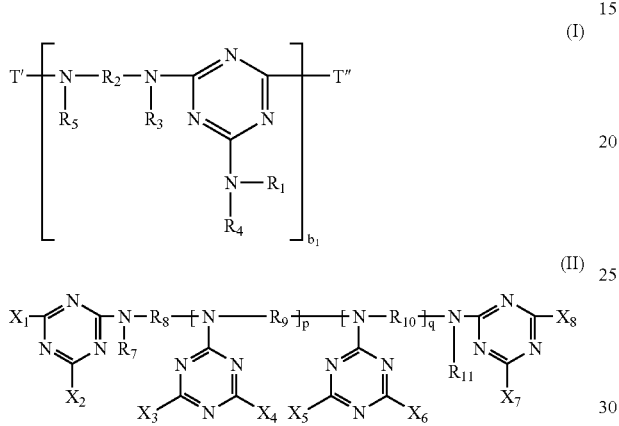

wherein in formula (I)

$R_1$, $R'_1$, $R_3$ and $R_5$ independently of one another are hydrogen, $C_1$–$C_{12}$alkyl, $C_5$–$C_{12}$cycloalkyl, $C_1$–$C_4$-alkyl-substituted $C_5$–$C_{12}$cycloalkyl, phenyl, phenyl which is substituted by —OH and/or $C_1$–$C_{10}$alkyl; $C_7$–$C_9$phenylalkyl or $C_7$–$C_9$phenylalkyl which is substituted on the phenyl radical by —OH and/or $C_1$–$C_{10}$alkyl;

$R_4$ is a group of formula (III),

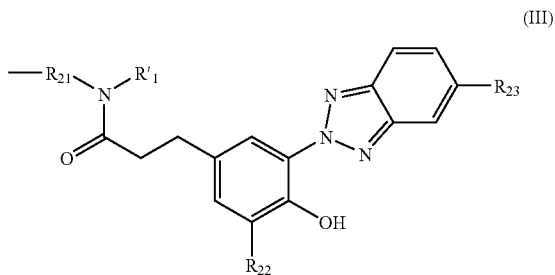

$R_2$ and $R_{21}$ are independently $C_2$–$C_{18}$alkylene, $C_5$–$C_7$cycloalkylene or $C_1$–$C_4$alkylenedi($C_5$–$C_7$cycloalkylene), or the radicals $R_5$, $R_2$ and $R_3$, together with the nitrogen atoms to which they are bound, perform a 5- to 10-membered heterocyclic ring, $b_1$ is a number from 2 to 50, $R_{22}$ is is hydrogen, straight or branched chain alkyl of 1 to 24 carbon atoms, straight or branched chain alkenyl of 2 to 24 carbon atoms, cycloalkyl of 5 to 12 carbon atoms, phenylalkyl of 7 to 15 carbon atoms, phenyl, or said phenyl or said phenylalkyl substituted on the phenyl ring by 1 to 4 alkyl of 1 to 4 carbon atoms; or $R_{22}$ is alkyl of 1 to 24 carbon atoms substituted by one or two hydroxy groups;

$R_{23}$ is hydrogen or halogen;

the terminal group T' is hydrogen or a group

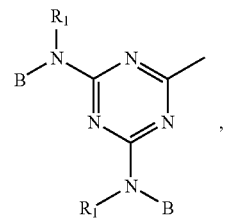

wherein B is a group of formula (III) and the terminal group T" is

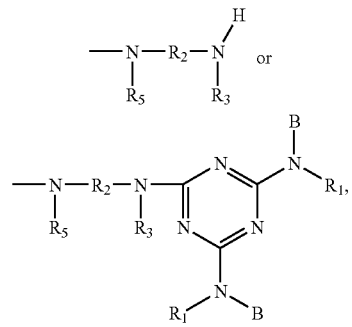

wherein in formula (II)

p and q are independently 0, 1 or 2;

with the proviso, that if p and q are both zero $X_1$, $X_2$, $X_3$ and $X_4$ are a group of formula —$NR_1B$;

$R_7$, $R_{11}$, $R_{12}$ and $R_{13}$ independently of one another are hydrogen or $C_1$–$C_{12}$alkyl, $R_8$, $R_9$ and $R_{10}$ independently of one another are $C_2$–$C_{10}$alkylene, and $X_1$, $X_2$, $X_3$, $X_4$, $X_5$, $X_6$, $X_7$ and $X_8$ independently of one another are a group —$NR_{12}R_{13}$ or —$NR_1B$ wherein B is a group of the formula (III) as defined above;

with the proviso that at least one triazine ring is substituted with a group —$NR_1B$.

2. A compound of formula (I) or (II) according to claim 1 wherein in the group of formula (III) $R_{22}$ is hydrogen, $C_7$–$C_9$-phenylalkyl or $C_1$–$C_8$alkyl.

3. A compound according to claim 1 wherein $R_1$, $R'_1$, $R_3$ and $R_5$ independently of one another are hydrogen, $C_1$–$C_{12}$alkyl or $C_5$–$C_6$cycloalkyl.

4. A compound according to claim 1 wherein $R_2$ and $R_{21}$ independently are $C_2$–$C_8$alkylene.

5. A compound according to claim 3 wherein $R_3$ and $R_5$ have the same meaning.

6. A compound according to claim 1 wherein b1 is a number from 2 to 25.

7. A compound according to claim 1 wherein $R_7$ and $R_{11}$ independently are hydrogen or $C_1$–$C_4$alkyl and $R_8$, $R_9$ and $R_{10}$ are $C_2$–$C_4$alkylene.

8. A plastic container or film which protects against the deleterious effects of ultraviolet radiation which comprises
   (a) a clear or lightly colored plastic, and
   (b) a compound of formula (I) or (II) according to claim 1.

9. A plastic container or film according to claim 8 which is a food packaging material.

10. A plastic container or film according to claim 8 wherein the clear or lightly colored plastic is a polyolefin, a polyester, a polyvinylalcohol, a polyvinylacetate or a polycarbonate.

11. A plastic container or film according to claim 8 wherein the thickness of the film is from 10μ to 200μ and the thickness of the plastic container from 200μ to 1000μ.

12. A plastic container or film according to claim 8 wherein the compound of formula (I) or (II) is present in an amount of from 0.005% to 10%.

13. A plastic container or film according to claim 8 which is a multilayer construction of between 2 and 7 polymer layers containing the compound of formula (I) or (II) in at least 1 layer.

14. A plastic container or film according to claim 8 which contains as additional additive a phenolic antioxidant, a sterically hindered amine, and/or a phosphite or phosphonite.

15. A plastic container or film according to claim 8 which contains as additional additive an iron based additive as oxygen absorber.

* * * * *